United States Patent [19]

Finke et al.

[11] Patent Number: 4,526,728
[45] Date of Patent: Jul. 2, 1985

[54] 2-ACRYLAMIDO- AND 2-METHACRYLAMIDO-2-METHYL PROPANEPHOSPHONIC ACIDS AND THEIR SALTS, PROCESS FOR THE PREPARATION THEREOF, AND USE THEREOF FOR THE MANUFACTURE OF COPOLYMERS

[75] Inventors: Manfred Finke, Kelkheim; Walter Rupp, Königstein; Erwin Weiss, Kelkheim, all of Fed. Rep. of Germany

[73] Assignee: Hoechst Aktiengesellschaft, Fed. Rep. of Germany

[21] Appl. No.: 596,895

[22] Filed: Apr. 5, 1984

Related U.S. Application Data

[63] Continuation-in-part of Ser. No. 477,142, Mar. 21, 1983, abandoned.

[30] Foreign Application Priority Data

Mar. 24, 1982 [DE] Fed. Rep. of Germany ....... 3210775
Apr. 16, 1983 [DE] Fed. Rep. of Germany ....... 3313819

[51] Int. Cl.$^3$ .................. C07F 9/38; C08G 63/00; C08G 63/44
[52] U.S. Cl. ............... 260/502.5 R; 528/271; 528/362; 528/363; 210/700; 260/502.4 R; 260/543 P
[58] Field of Search ................ 260/502.5 R

[56] References Cited

U.S. PATENT DOCUMENTS 2,993,067  7/1961  Magerlein et al. ........... 260/502.5 R
3,812,221  5/1974  Braden et al. ................ 260/502.5 R
4,213,969  7/1980  Baylis et al. ................. 260/502.5 R

*Primary Examiner*—J. E. Evans
*Attorney, Agent, or Firm*—Connolly and Hutz

[57] ABSTRACT

2-(Meth)acrylamido-2-methylpropanephosphonic acid is prepared by reaction of 2-methylprop-1-ene-1-phosphonic acid or 2-methylpro-2-ene-1-phosphonic acid with (meth)acrylonitrile in the presence of an equimolar amount of a strong acid. The compounds are suitable as such or in the form of their salts as comonomer for the manufacture of copolymers, which are used inter alia as dyeing auxiliaries and as scale inhibitors.

1 Claim, No Drawings

2-ACRYLAMIDO- AND 2-METHACRYLAMIDO-2-METHYL PROPANEPHOSPHONIC ACIDS AND THEIR SALTS, PROCESS FOR THE PREPARATION THEREOF, AND USE THEREOF FOR THE MANUFACTURE OF COPOLYMERS

This is a continuation-in-part-application of application Ser. No. 477,142, filed Mar. 21, 1983 by Finke et al, now abandoned.

Acryl- and Methacrylamidoalkanesulfonic and -phosphonic acids are known (European Pat. No. 10,355). Because there is interest in similar polymerizable phosphonic acids having corresponding improved properties for use in the industrial practice, especially an increased stability to hydrolysis of the amide bond, 2-acrylamido- and 2-methacrylamido-2-methyl-propanephosphonic acid are prepared which hitherto were unkown.

Subject of the invention are 2-(meth)acrylamido-2-methyl-propanephosphonic acid of the formula

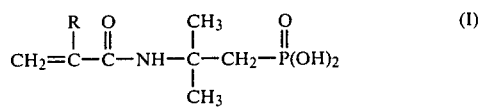

and the salts thereof, wherein R is hydrogen or methyl.

The 2-(meth)acrylamido-2-methylpropanephosphonic acid is prepared according to the principle of the Ritter reaction from (meth)acrylonitrile and 2-methyl-prop-1-ene-1-phosphonic acid or isomeric 2-methyl-prop-2-ene-1-phosphonic acid, or mixtures of the two phosphonic acids, in the presence of strong acids such as $H_2SO_4$, $H_3PO_4$, $HClO_4$, HF, according to the following reaction scheme:

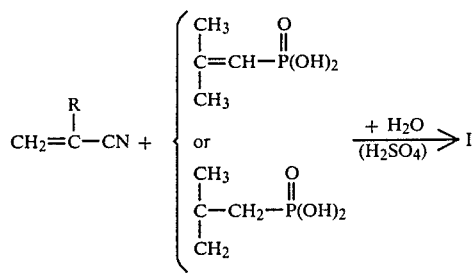

The 2-methyl-prop-1-ene- or 2-methyl-prop-2-ene-phosphonic acids used are easily obtainable by hydrolysis of the corresponding phosphonic acid dichlorides, which 2-methylpropene-1-phosphonic acid dichlorides are already described in detail in the literature (U.S. Pat. No. 2,471,472; L. Maier, Phosphorus 5, 223 (1975)).

The isomer mixture of the 2-methyl-propene-1-phosphonic acids is reacted with (meth)acrylonitrile in a molar ratio of about 1:1. An additional solvent is not necessary; however, an excess of the strong acid or of methacrylonitrile required for the reaction may serve as a solvent.

The reaction temperatures are from 10° to 90° C.; preferably, the temperature is raised during the reaction from about room temperature to about 60°–70° C. towards the end. The reaction time ranges from 1 hour to several days; preferably, it is from 12 to 24 hours.

Suitable strong mineral acids are those cited above and sulfonic acid group-containing ion exchangers, generally in aqueous form; preferably, concentrated sulfuric acid is used which contains the one equivalent of water required for the reaction. The mineral acid is used in an amount at least equimolar to that of the starting compounds.

The salts of the phosphonic acid I are prepared according to known methods, for example by reaction with equivalent amounts of a metal hydroxide or carbonate from an aqueous or alcoholic solution.

Suitable metal hydroxides are alkali or alkali earth metal hydroxides, zinc, aluminum or iron hydroxides, especially sodium or potassium hydroxide, or ammonium hydroxides optionally substituted by $(C_1-C_4)$-alkyl, especially ammonium hydroxide.

Salts of the compounds I according to the invention are for example: monosodium, monopotassium, monolithium, monoammonium, magnesium, calcium, aluminum, zinc, iron, disodium and dipotassium salt. The compounds of the formula I and their salts are extremely stable to hydrolysis and are valuable monomers for the manufacture of copolymers. Thus, copolymers of 2-(meth)acrylamido-2-methylpropanephosphonic acid and acrylonitrile have a reduced flammability. Copolymers with acrylamide can be applied as dyeing auxiliaries, and copolymers with acrylic acid may be used as scale inhibitors.

The following examples illustrate the invention.

EXAMPLE 1

1041 g (5 mols) of $PCl_5$ were suspended in 2.5 l of anhydrous toluene, and 281 g (5 mols) of isobutene were introduced at 10°–15° C. The batch was stirred for 30 minutes at 15° C., and subsequently $SO_2$ was introduced at 10°–15° C. until a clear solution has formed.

Toluene and $SOCl_2$ were distilled off. In order to split off the hydrogen chloride, the residue was heated for 8 hours at 270 mbar and 180° C. with addition of 3 g of triphenylphosphane.

Distillation yielded 550 g of a mixture of the isomeric 2-methyl-propene-phosphonic acid dichlorides. B.p. at 16 mbar: 90°–93° C. Yield: 64%.

173 g (1 mol) of 2-methylpropene-phosphonic acid dichloride are added dropwise to 200 ml of water at 20° C. Subsequently, the batch is evaporated in vacuo, and dehydrated in vacuo with toluene as an azeotropic mixture. The toluene is distilled off under reduced pressure and the remaining free phosphonic acid is mixed with 53.5 g (1 mol) of acrylonitrile. 104 g (1 mol) of 96% sulfuric acid are added dropwise to this mixture at 25°–30° C. After 24 hours, 100 g of ice are added to the reaction mixture, and the sulfuric acid is neutralized with 80 g of NaOH in 200 ml of water. The batch is evaporated to dryness in vacuo, the salt residue is extracted with isobutanol, concentrated, and the 2-acrylamido-2-methyl-propane-phosphonic acid I is precipitated with acetone.

Yield: 87 g (42% of theory)
M.p.: 148°–150° C.

EXAMPLE 2

500 g (2.89 mols) of 2-methyl-propene-phosphonic acid dichloride (isomer mixture prepared according to Example 1) are hydrolyzed at 20° C. with 231 g (5.78 mols) of sodium hydroxide in 600 ml of water, and the mixture is completely evaporated in vacuo. 1,000 ml of acetone are added, sodium chloride is filtered off, and the batch is washed twice with 500 ml each of acetone. The solvent is distilled off, and the residue is completely dried at 50° C. under highly reduced pressure. 388 g (98.5% of theory) of 2-methyl-propane phosphonic acid (isomer mixture) are obtained.

388 g (2.85 mols) of 2-methyl-propene-phosphonic acid (isomer mixture) are suspended in 166 g (3.13 mols) of acrylonitrile (10% excess), 3 g of phenothiazine are added, and a mixture of 288 g (2.85 mols) of sulfuric acid (97% strength) and 51 g (2.85 mols) of water is added dropwise with ice cooling. The mixture is first maintained for 16 hours at 25°–30° C., then heated within 4 hours to 60° C., and this temperature is maintained for a further 16 hours.

Excess acrylonitrile is distilled off under reduced pressure, the very viscous reaction mass is dissolved in 2,000 ml of water, and 285 g (2.85 mols) of calcium carbonate are added. The batch is filtered, washed twice with 500 ml each of water, and the filtrate is completely evaporated. The residue is washed with acetone. 486 g (79% of theory) of 2-(N-acrylamido)-2-methyl-propanephosphonic acid are obtained as a white powder. M.P.: 148°–150° C.

EXAMPLE 3

500 ml of deionized water are introduced into a reaction vessel (volume 2 liters) provided with agitator, reflux condenser, gas inlet tube and electrically heated water bath, and with stirring and introduction of nitrogen 70 g of acrylamide and 10 g of 2-acrylamido-2-methylpropanephosphonic acid are dissolved.

5 ml of isopropanol are added, and the temperature in the flask is then raised to 70° C. Next, a solution of 0.25 g of ammonium peroxodisulfate in 10 ml of water is added dropwise within 10 minutes, thus raising the temperature of the reaction mixture to 78° C. After decrease of the temperature agitation is continued for 2 hours at a bath temperature of 80° C. A clear, viscous solution having a pH of 2.1 and a Brookfield viscosity of 14,383 cp is obtained.

A fabric consisting of 50% of polyester and 50% of cotton was impregnated on a foulard at a liquor uptake of 60% with a liquor consisting of
15 g of dyestuff Disperse Red 90,
15 g of dyestuff C.I. Vat Red 51
10 g of the polymer solution prepared as indicated above
460 g of water,
and then dried on a stenter. A dying was obtained with the same color depth on the upper and lower side of the fabric.

EXAMPLE 4

A copolymer of 50 weight parts of 2-methacrylamido-2-methylpropanephosphonic acid and 50 weight parts of acrylic acid was prepared by radical initiated solution polymerization in a water/isopropanol mixture at 85° C.

The resulting copolymer having a k value of 23 (according to Fikentscher) was tested according to NACE standard TM-03-74 (NACE=National Association of Corrosion Engineers, 1440 South Creek, Houston, Tex.) as scale inhibitor for the prevention of calcium sulfate and calcium carbonate precipitates in aqueous solutions.

With addition of 10 ppm of polymer according to the test prescription, a commercial product having the trade name ®ACRYLRON A 002 of Messrs. PRO-TEX was tested against a copolymer of the invention having the composition as above.

|  | Copolymer of I + acrylic acid | (R)Acrylron A 002 |
|---|---|---|
| Ca sulfate retention value | 5120 mg/l | 3833 mg/l |
| Ca carbonate retention value | 3819 mg/l | 2965 mg/l |

EXAMPLE 5

1041 g (5 mols) of $PCl_5$ were suspended in 2.5 l of anhydrous toluene, and 281 g (5 mols) of isobutene were introduced at 10°–15° C. The batch was stirred for 30 minutes at 15° C., and subsequently $SO_2$ was introduced at 10°–15° C. until a clear solution has formed.

Toluene and $SOCl_2$ were distilled off. In order to split off the hydrogen chloride, the residue was heated for 8 hours at 270 mbar and 180° C. with addition of 3 g of triphenylphosphane.

Distillation yielded 660 g of a mixture of the isomeric 2-methyl-propene-phosphonic acid dichlorides. B.p. at 16 mbar: 90°–93° C. Yield: 76.3%.

500 g (2.89 mols) of 2-methylpropene-phosphonic acid dichloride were added dropwise to a solution of 231 g (5.78 mols) of sodium hydroxide in 600 ml of water at 20° C. Subsequently, the batch was concentrated by evaporation in vacuao and the remaining phosphonic acid was extracted with 1,000 ml of acetone. The sodium chloride residues were after-washed with 2 by 500 ml portions of acetone, the combined filtrates were concentrated by evaporation and finally dried for 4 hours in a high vacuum at 50° C.

Yield: 388 g (98.5% of the theory).

0.5 g of phenothiazine and 98 g (1.47 mol) of methacrylonitrile were added to 100 g (0.735 mol) of the above obtained 2-methyl-propene-phosphonic acid (mixture of isomers) and a mixture of 75.8 g (0.735 mol) of 97% sulfuric acid and 13.2 g (0.735 mol) of water was added dropwise at 20°–30° C. The reaction mixture was kept at 25°–30° C. for 16 hours, heated to 60° C. over a period of 4 hours and maintained at 60° C. for a further 16 hours. The cooled residue was suspended in 500 ml of water, 58.8 g (1.47 mol) of sodium hydroxide in 100 ml of water were added and the water was substantially distilled off in vacuo. The residue was extracted with 3 250 ml portions of isobutanol, the isobutanol phase was concentrated by evaporation and 2-methacrylamido-2-methyl-propanephosphonic acid was precipitated by addition of 1,000 ml of acetone.

Yield: 109 g=67% of the theory, M.p.: 149°–151° C.

EXAMPLE 6

200 mg of phenothiazine and 22.1 g (0.33 mol) of methacrylonitrile were added to 45 g (0.33 mol) of 2-methylpropene-phosphonic acid (according to Example 5). A mixture of 33.3 g (0.33 mol) of 97% sulfuric acid and 5.9 g (0.33 mol) of water was added dropwise at 20° C. After having kept the batch for 16 hours at 20°–30° C., the temperature was raised to 60° C. within 4 hours and this temperature was maintained for a further 16 hours. The cooled reaction batch was dissolved in a mixture of 21 g of water and of 200 ml of methanol and the sulfuric acid was neutralized by adding a solution of 26.4 g (0.66 mol) of NaOH, 21 ml of water and 200 ml of methanol. Sodium sulfate was filtered off and the filtrate was concentrated by evaporation. 2-Methacrylamido-2-methyl-propane-phosphonic acid was precipitated by adding 250 ml of acetone.

Yield: 44.3 g (60.5% of the theory).

EXAMPLE 7

500 ml of de-ionized water were given into a 2 l polymerization flask provided with a stirrer, a reflux condenser, a gas inlet tube and an electrically heated water bath and 80 g of acrylamide and 10 g of 2-methacrylamido-2-methylpropane-phosphonic acid (MAMPP) were dissolved therein while stirring and introducing nitrogen. After addition of 5 ml of isopropanol the temperature in the flask was raised to 70° C. A solution of 0.25 g of ammonium peroxodisulfate in 10 ml of water was added dropwise within 10 minutes. whereby the temperature of the reaction mixture rised to 75° C. After the temperature had dropped, stirring was continued for 2 hours at a bath temperature of 80° C. A clear viscous solution having a pH of 2.21 and a viscosity according to Brookfield of 12172 cp was obtained.

A fabric consisting of 50% of polyester and 50% of cotton was impregnated on a foulard at a liquor uptake of 60% with a liquor consisting of 15 g of dyestuff Disperse Red 90, 15 g of dyestuff Vat Red 51, 10 g of the polymer solution prepared as indicated above and 960 g of water, and then dried on a stenter. A dying was obtained with the same color depth on the upper and lower side of the fabric.

EXAMPLE 8

A copolymer of 50 weight parts of 2-methacrylamido-2-methylpropanephosphonic acid and 50 weight parts of acrylic acid was prepared by radical initiated solution polymerization in a water/isopropanol mixture at 85° C.

The resulting copolymer having a k value of 18 (according to Fikentscher) was tested according to NACE standard TM-03-74 (NACE=National Association of Corrosion Engineers, 1440 South Creek, Houston, Tex.) as scale inhibitor for the prevention of calcium sulfate and calcium carbonate precipitators in aqueous solutions.

With addition of 10 ppm of polymer according to the test prescription, a commercial product having the trade name ®ACRYLON A 002 of Messrs. PROTEX was tested against a copolymer of the invention having the composition as above.

|  | Copolymer of MAMPP - acrylic acid | (R)Acrylon A 002 |
| --- | --- | --- |
| Ca sulfate retention value | 4872 mg/l | 3833 mg/l |
| ca carbonate retention value | 3711 mg/l | 2965 mg/l |

What is claimed is:

1. Acrylamido- and Methacrylamido-2-methylpropanephosphonic acids of the formula

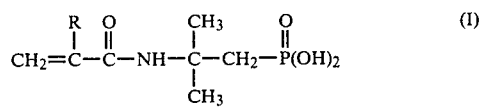

and the salts thereof wherein R is hydrogen or methyl.

* * * * *